United States Patent [19]

Holm

[11] Patent Number: 5,376,079

[45] Date of Patent: Dec. 27, 1994

[54] DISPENSING DEVICE FOR DISPENSING AT LEAST TWO FLUIDS

[76] Inventor: Niels E. Holm, Julmosevej 10B, 3460 Birkerod, Denmark

[21] Appl. No.: 66,020

[22] PCT Filed: Sep. 30, 1992

[86] PCT No.: PCT/DK92/00287

§ 371 Date: May 25, 1993

§ 102(e) Date: May 25, 1993

[87] PCT Pub. No.: WO93/06940

PCT Pub. Date: Apr. 15, 1993

[30] Foreign Application Priority Data

Sep. 30, 1991 [DK] Denmark ............... 1666/92

[51] Int. Cl.$^5$ ............................................. A61M 5/00
[52] U.S. Cl. ...................................... 604/191; 604/209; 604/82
[58] Field of Search ............... 222/137, 327, 391; 604/61, 82, 191, 207, 209, 246

[56] References Cited

U.S. PATENT DOCUMENTS

| | | |
|---|---|---|
| 1,595,424 | 8/1926 | Sather . |
| 3,223,083 | 12/1965 | Cobey . |
| 3,517,668 | 6/1970 | Brickson ............... 604/209 |
| 3,905,365 | 9/1975 | Colombo ............... 604/209 |
| 4,359,049 | 11/1982 | Redl et al. . |
| 4,364,388 | 12/1982 | Cech . |
| 4,452,285 | 6/1984 | Leibhard et al. . |
| 4,471,888 | 9/1984 | Herb et al. ............... 222/391 X |
| 4,526,303 | 7/1985 | Harrod . |
| 4,566,610 | 1/1986 | Herb ............... 222/391 X |
| 4,581,022 | 4/1986 | Leonard et al. . |
| 4,655,372 | 4/1987 | Ross et al. . |
| 4,666,429 | 5/1987 | Stone . |
| 4,690,306 | 9/1987 | Staheli . |
| 4,710,178 | 12/1987 | Leonard et al. . |
| 4,784,157 | 11/1988 | Halls et al. . |
| 4,795,441 | 1/1989 | Bhatt . |
| 4,902,281 | 2/1990 | Avoy ............... 604/191 |
| 4,934,827 | 6/1990 | Taschke et al. ............... 222/137 X |
| 4,994,065 | 2/1991 | Gibbs et al. ............... 604/61 X |
| 5,065,906 | 11/1991 | Maeder . |
| 5,137,181 | 8/1992 | Keller ............... 222/327 X |

FOREIGN PATENT DOCUMENTS

| | | |
|---|---|---|
| 2000659 | 4/1990 | Canada . |
| 2021044 | 1/1991 | Canada . |
| 54156 | 6/1982 | European Pat. Off. . |
| 109913 | 5/1984 | European Pat. Off. . |
| 363967 | 4/1990 | European Pat. Off. . |
| 408494 | 1/1991 | European Pat. Off. . |
| 3234250 | 3/1984 | Germany . |
| 3602975 | 8/1987 | Germany . |
| 3903315 | 8/1989 | Germany ............... 604/191 |
| 3903305 | 8/1990 | Germany . |
| 3920694 | 1/1991 | Germany ............... 222/137 |
| 2227649 | 8/1990 | United Kingdom . |
| WO87/04645 | 8/1987 | WIPO . |
| WO88/02259 | 4/1988 | WIPO . |

Primary Examiner—C. Fred Rosenbaum
Assistant Examiner—Frank Wilkens
Attorney, Agent, or Firm—Willian Brinks Hofer Gilson & Lione

[57] ABSTRACT

A dispensing device for dispensing at least two fluids comprises a housing (12,22) of a pistol-like configuration having an integral handle (50), in which a spring-biased trigger (60) is received. Within the housing (12,22) of the dispensing device (10), two syringes (80,81) are received and fixated, which syringes contain respective fluids to be accurately dispensed. Provided a cover (22) of the housing is closed, the motion of the trigger (60) relative to the handle (50) is transmitted to a toothed rack which cooperates with a propeller body (70) in a ratchet-like manner. The ratchet-like cooperation allows a uni-directional motion of the propeller body (70) and prevents a motion of the propeller body (70) in the opposite direction. Provided the cover (22) is not closed, the motion of the trigger (60) relative to the handle is not transmitted to the propeller body (70), and any unintentional dispensing of fluids from the dispensing device prior to the preparing of the dispensing device for use by closing the cover (22) is consequently prevented.

23 Claims, 8 Drawing Sheets

DISPENSING DEVICE FOR DISPENSING AT LEAST TWO FLUIDS

BACKGROUND OF THE INVENTION

The present invention relates to a dispensing device for dispensing at least two fluids. More precisely, the present invention relates to a manually operated dispensing device for dispensing two or more fluids which are contained within respective syringes which are received and supported by the dispensing device.

In the present context, the term "fluid" means a liquid or a substance which is pourable and in a liquefied state as distinct from a gaseous state.

Published international patent application, Publication No. WO 88/02259 discloses a technique of preparing tissue repair promoting substances, which substances are later on applied for tissue repair by means of two separate syringes which are to be operated simultaneously. The two separate syringes contain fibrinogen extracted from blood of a person or patient and a suitable enzyme, such as thrombin, respectively. The fibrinogen and thrombin form together, like in nature, fibrin which is an insoluble network of fiber-like material constituting a kind of tissue glue interconnecting a wound to be repaired. The healing glue also has favourable effect on the process of healing the wound. The tissue glue is advantageously used after surgery.

The technique of dispensing two components from a syringe assembly comprising two separate syringes which are to be operated simultaneously, however, is by no means advantageous as the two syringes are more difficult to operate than a single syringe and further as the initial frictional force of the two syringes far exceed the frictional force to be exceeded when using a single syringe for dosing a small amount of material from both syringes. Therefore, the technique of applying materials from two syringes which are operated simultaneously inevitably results in an inaccurate dosing of the materials and also in that excessive materials are dispensed from the syringes as an accurate and small amount dosing is simply impossible. The dispensing of excessive materials from the syringes is for numerous reasons inadequate and not advantageous as materials are wasted, which materials are often highly expensive.

As far as the technique of preparing tissue repair constituents or substances is concerned, reference is made to the above published international patent application.

Manually operated dispensing devices for dispensing materials from two or more syringes are also known within the art. Examples of such dispensing devices are disclosed in U.S. Pat. No. 4,690,306, published European patent application No. 0 363 967, published European patent application No. 0 408 494, published German patent application No. 32 34 250, published German patent application No. 36 02 975, and published German patent application No. 39 03 305. Reference is made to the above-mentioned patents and published patent applications, and the above-mentioned U.S. patent is further incorporated in the present specification by reference.

Common to the prior art dispensing devices for manually dispensing or dosing two or more fluids is the fact that the dispensing devices are not adapted to dispense small amounts of fluids in exactly dosed amounts. A further drawback relates to the initial frictional forces of the dispensing devices which result in that a fairly high initial frictional threshold has to be exceeded for dispensing the fluids which renders it difficult to dispense small amounts of fluids by means of the dispensing devices according to the prior art at small or fairly small operational power or pressure levels, such as pressure or power levels generated manually by e.g. a person of the staff of a hospital, such as a doctor or a nurse.

An object of the present invention is to provide a manually operated dispensing device for dispensing at least two fluids, by means of which dispensing device small amounts of fluids may be accurately dispensed or dosed in exact amounts and at small operational power levels.

A further object of the present invention is to provide a manually operated dispensing device for dispensing at least two fluids which is easily manually operable by a person.

An advantage of the present invention resides in the fact that a manually operated dispensing device is provided comprising a minimum set of components which may be manufactured from low-cost materials rendering it possible to produce a fairly cheap, yet easily operable and exact dosing or dispensing device.

A particular feature of the present invention relates to the fact that the manually operated dispensing device according to the present invention is prevented from unintentionally dispensing fluids prior to the intentional use of the dispensing device which efficiently prevents the unintentional waste of materials or fluids.

The above objects, the above feature, and the above advantage are, together with numerous other objects, features, and advantages which will be evident from the below description, obtained in accordance with the teachings of the present invention by means of a dispensing device for dispensing at least two fluids, comprising:

housing means of a pistol-like configuration defining an inner space for receiving and fixating a first and a second syringe containing a first and a second fluid, respectively, each of said syringes comprising:

a syringe housing of an elongated configuration defining opposite proximal and distal ends, a piston rod received within said syringe housing and defining together therewith a syringe chamber in which said fluid is confined, said piston rod protruding from said proximal end, and a dispensing aperture being provided at said distal end, said dispensing aperture communicating with the surroundings relative to said inner space of said housing means, handle means constituting a component of said housing means and including a manually operable, spring-biased trigger means movable relative to said handle means from an inactive position to an active position, propeller means received within said inner space of said housing means and movable relative thereto for moving said piston rods of said syringes from said proximal ends towards said distal ends for dispensing said fluids from said syringes, transmission means switchable between a disengaged and an engaged position for transmitting the motion of said trigger means to said propeller means as said trigger means is moved from said inactive position to said active position for generating a uni-directional motion of said piston rods from said proximal ends towards said distal ends, provided said transmission means are in said engaged position and for preventing the transmission of the motion generated by said trigger means, provided said transmission means are in said disengaged position, and switch means received by said housing means switchable between a first and a second position, in which first position said transmission means is in said disengaged position, and in which second position said transmission means is in said engaged position.

The dispensing device according to the present invention may be employed for manually dispensing two or more sets of fluids which are to be mixed prior to use, such as adhesives or glues to be composed of two or more constituents, or drugs also to be composed of two or more constituents. The dispensing device according to the present invention is preferably used for dispensing tissue glue, e.g. the tissue glue or tissue repair promoting substances disclosed in the above-mentioned international patent application, Publication No. WO 88/02259.

In accordance with the teachings of the present invention, a dispensing device is provided, comprising propeller means, transmission means, and switch means housed by a housing means of the dispensing device, which housing means also receives and fixates two or more syringes containing the fluids to be dispensed by means of the dispensing device. The propeller means of the dispensing device may be constituted by any appropriate means serving the purpose of propelling the piston rods of the syringes from the proximal ends towards the distal ends of the syringes for dispensing the liquids from the syringes. The propeller means may be propelled in any motion, such as a linear motion, a rotational motion, or any combination thereof. Preferably, the propeller means is adapted to perform a linear displacement or longitudinal motion relative to the housing means of the dispensing device for displacing the piston rods of the syringes.

The transmission means of the dispensing device according to the present invention serves the purpose of transmitting the motion of the trigger means to the propeller means for generating a uni-directional motion of the propeller means, and consequently the piston rods, provided the transmission means are in an engaged position. In the present context, the term "a uni-directional motion" is to be construed as comprising any motion according to which the main motional direction is uni-directional which means that the propeller means, and consequently the pistons of the syringes are moved in a single direction. The term "uni-directional", thus, implies that the motion in question is performed in a single direction from an initial position to an intentional position and implies that a reversal of the direction of motion is prevented. Thus, the transmission means of the dispensing device according to the present invention prevents the motion or displacement of the piston rods of the syringes being reversed.

The switch means of the dispensing device according to the present invention may be constituted by any separate or integral appropriate part, component or means of the dispensing device, such as a separate switch, a separate component fulfilling the purpose of switching the transmission means of the dispensing device from disengaged to engaged position and, if appropriate, vice versa.

According to the presently preferred embodiment of the dispensing device according to the present invention, the switch means is constituted by a cover of the housing means, which cover is shiftable from an open position to a closed position, which open position constitutes the first position, and which closed position constitutes the second position of the switch means. Consequently, as the cover of the housing means constituting the switch means is closed, the transmission means is engaged, allowing the dispensing of the two or more fluids from the syringes of the dispensing device.

The cover may constitute a separate component of the housing means of the dispensing device, or preferably constitute an integral component of the housing means of the dispensing device, which cover in the second position seals the inner space of the housing means fully or partially so as to fully or partially conceal the syringes within the inner space of the housing means. Thus, it may be preferable to leave the distal ends of the syringes free for inspection to give the operator a warning of the approaching emptying of the syringes. The syringes may be of identical structure or different structure and may be of identical or different volumetric capacity, f. inst. of different cross-sectional area. Also, the distance of displacement of the piston rods of the syringes may be identical or different, in which first instance the propeller means of the dispensing device according to the present invention may be constituted by a single propeller means, whereas in the second instance, the propeller means of the dispensing device preferably comprise separate first and second propeller means cooperating with the first and the second syringe, respectively.

Provided the propeller means comprise separate first and second propeller means, the transmission means of the dispensing device also preferably comprises separate first and second transmission means cooperating with the first and the second propeller means, respectively, in order to transmit the motion of the trigger means to the first and second propeller means, respectively.

By providing separate first and second transmission means cooperating with the first and second propeller means, respectively, it is rendered possible to dispense one of the fluids from one of the syringes independent of the dispensing of the fluid from the other syringe. Thus, in some instances, it is advantageous and desirable to add a small amount of one of the fluids to a mixture which is rendered possible by separately activating one of the transmission means independent of the other transmission means for causing the propeller means cooperating with the transmission means in question to generate a uni-directional motion of the piston rod of one of the syringes towards the distal end of the syringe in question, still provided the transmission means is in the engaged position.

The mixture of the two or more fluids is characterized by a ratio of mixture, and more precisely a ratio determined by the amount of one of the fluids as compared to the amount of the other fluid of the mixture. The dispensing device according to the present invention renders it possible to dispense two or more fluids of a constant ratio of mixture of the two or more fluids. Provided the syringes containing the two or more fluids in question are of different structure, the ratio of mixture is determined by the cross-sectional areas of the syringes in question, exclusively, provided a single propeller means is employed. In case separate transmission means and separate propeller means are employed, the ratio of mixture is furthermore determined by the ratio of transmission of the transmission means in question, and consequently of the ratio of displacement of the piston rods of the syringes caused by the activation of the spring-biased trigger means of the dispensing device. Provided separate first and second transmission means cooperating with separate first and second propeller means are provided, the ratio of transmission of one of the transmission means, or both transmission means, may be adjusted for adjusting or altering the ratio or mixture of the two fluids dispensed by the dispensing means by adjusting the transmission means which are constituted by adjustable transmission means.

The transmission means being common or independent transmission means cooperating with a single propeller means or independent propeller means may be constituted by any appropriate transmission means allowing a uni-directional motion of the piston rods from the proximal ends to the distal ends thereof. The transmission means may e.g. be constituted by frictional transmission means or preferably be constituted by ratchet means. Further preferably in accordance with the presently preferred embodiment of the dispensing device according to the present invention, the ratchet means comprise toothed rack means cooperating with the propeller means for generating the uni-directional motion of the propeller means. Alternatively, the ratchet means may comprise toothed wheels or toothed wheels cooperating with toothed ratchets or additionally comprising frictional means or any additional motion transmission or motion directional means.

In accordance with a particular aspect of the present invention, the propeller means comprises a single propeller body provided with recesses for receiving the piston rods of the syringes. The propeller body further preferably is provided with recesses allowing the piston rods of the two syringes to be arranged or received by the propeller body from opposite sides of the propeller body, allowing an extremely adequate and simple technique of mounting the syringes relative to the dispensing device. Thus, the syringes may constitute integral or separate components of the dispensing device and, provided the syringes constitute separate components, the syringes may contain fluids of e.g. highly different cost or highly different toxicity. In case the fluids contained within the two syringes are different, and further provided the two fluids are to be handled in accordance with different routines, taking into due consideration the difference of cost or toxicity of the two fluids, the provision of a propeller body having recesses for receiving and cooperating with the piston rods of the two syringes from separate or opposite sides renders it possible to arrange and mount the syringes within the dispensing device by firstly arranging the syringe containing the less expensive or less toxic fluid within the dispensing device and adjusting the propeller body relative to the syringe in question and secondly arranging the syringe containing the most expensive or most toxic fluid within the dispensing device and adjust the position of the propeller body relative to the housing means by dispensing or wasting the less expensive or less toxic fluid from the dispensing device without wasting any of the more expensive or more toxic fluid.

BRIEF DESCRIPTION OF THE DRAWINGS

The present invention will now be further described with reference to the drawings, in which.

DETAILED DESCRIPTION OF THE PREFERRED EMBODIMENT

Figure 1:
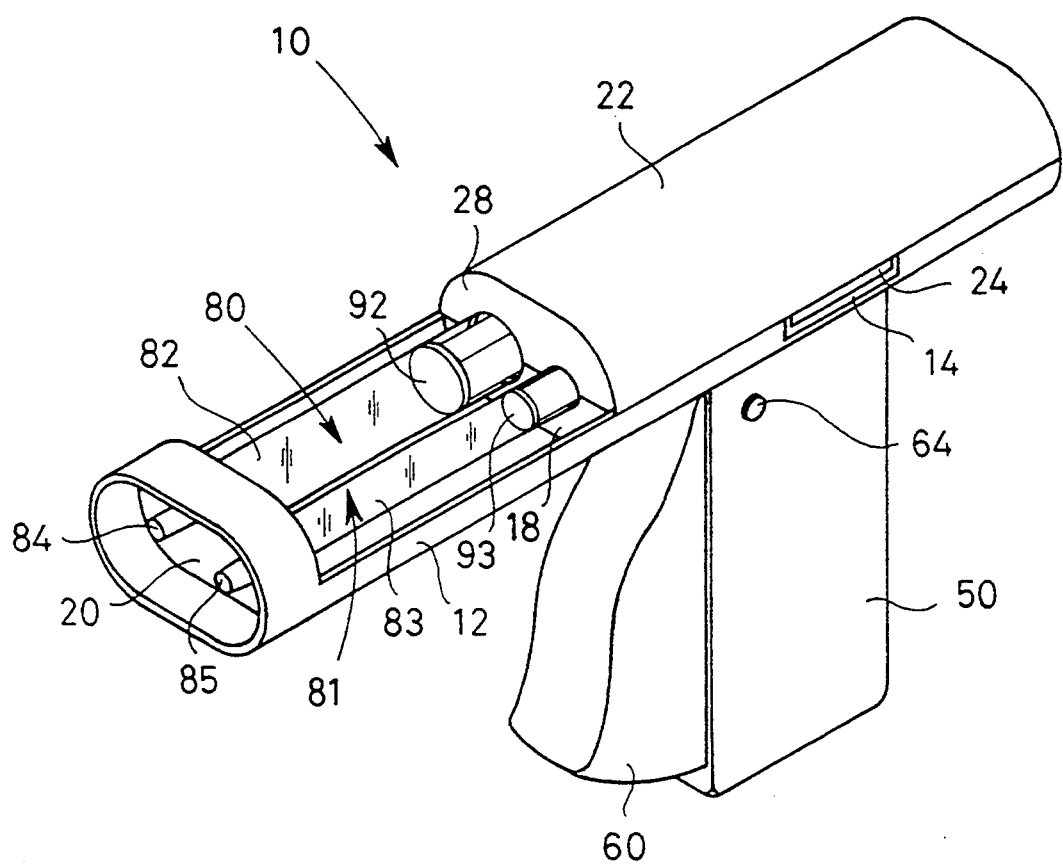
FIG. 1 is a perspective and schematical view of a first and presently preferred embodiment of a dispensing device according to the present invention.
Figure 2:
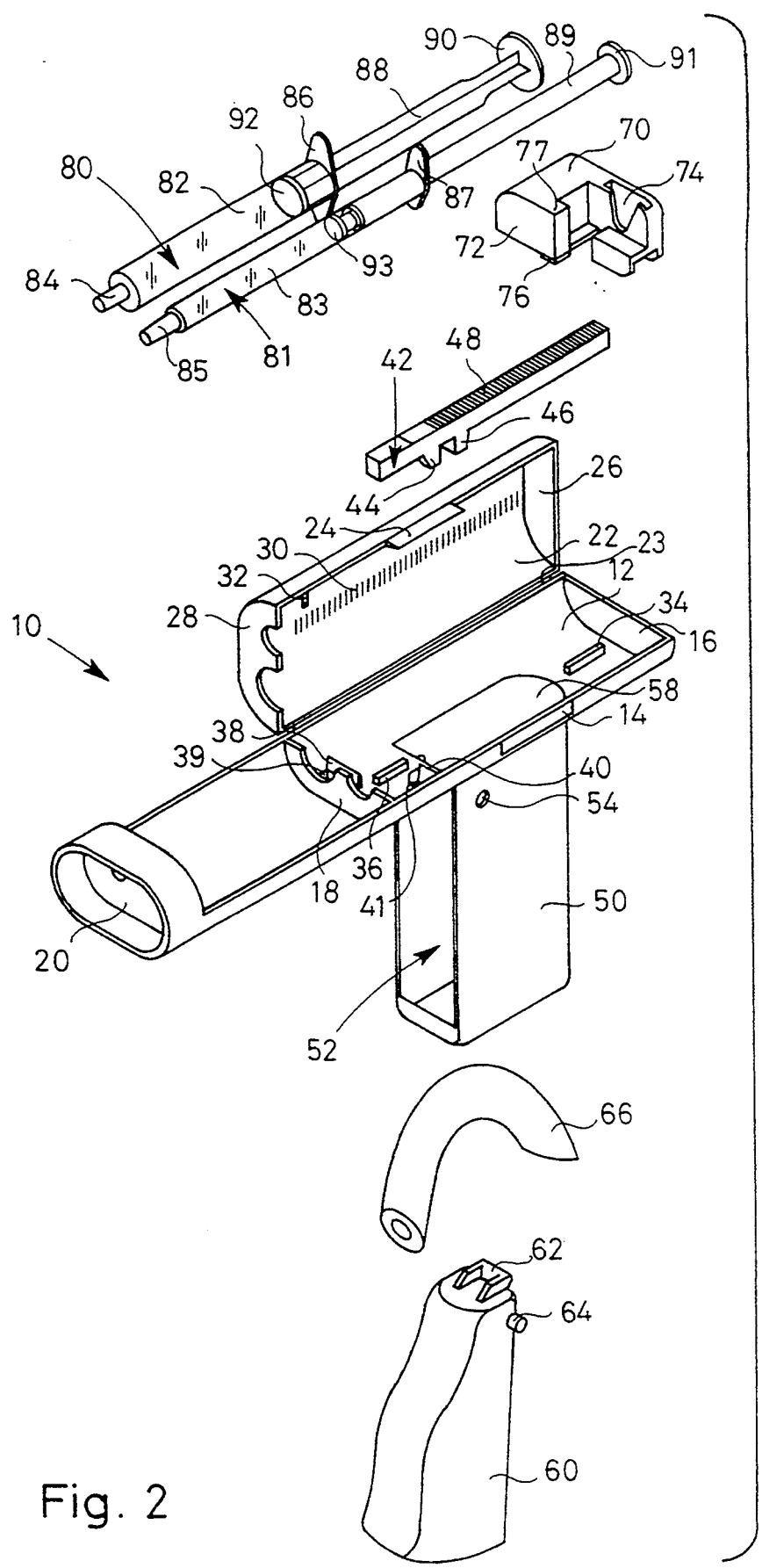
FIG. 2 is an exploded, perspective and schematical view of the first and presently preferred embodiment of the dispensing device according to the present invention also shown in FIG. 1.

In FIGS. 1 and 2, a first, and presently preferred embodiment, of a dispensing device implemented in accordance with the teachings of the present invention is shown, designated by the reference numeral 10 in its entirety. The dispensing device 10 comprises a housing including a trough-shaped housing part 12 which serves the purpose of receiving and supporting two syringes 80 and 81 containing respective fluids, i.e. fluids such as solutions of fibrinogen and thrombin, which are to be accurately dispensed from the syringes in specific amounts and are to be mixed with one another for generating a mixture forming a so-called tissue glue. The housing of the dispensing device 10 further comprises a cover or lid 22 which is connected to the trough-shaped housing part 12 along a foil hinge 23. The trough-shaped housing part 12 further comprises a rear wall 16, a partition wall 18 which is provided with semi-circular cuts serving the purpose of receiving the outer surfaces of the syringes 80, 81, and a front wall 20. The cover or lid only covers a part of the trough-shaped housing part 12 leaving the major parts of the syringes 80 and 81 free for inspection by an operator.

The cover or lid 22 is, like the trough-shaped housing part 12, provided with a rear wall 26 and a front wall 28 which, like the partition wall 18 of the trough-shaped housing part 12, is provided with semi-circular cuts serving the same purpose as the cuts of the partition wall 18. The semi-circular cuts of the partition wall 18 and the front wall 28 of the trough-shaped housing part 12 and the cover or lid 22, respectively, together constitute circular through-going holes as the cover or lid 22 is in its closed position as shown in FIG. 1, which holes are arranged in registration with holes of the front wall 20 of the trough-shaped housing part 12. For fixating the cover or lid 22 in its closed position, as shown in FIG. 1, the cover or lid 22 is provided with a locking component 24 which is adapted to cooperate with an arresting recess 14 of the trough-shaped housing part 12.

The trough-shaped housing part 12 is integrally connected to a handle 50 as the trough-shaped housing part 12, the cover or lid 22, and the handle 12 are integrally cast from a plastics material, such as preferably impact-resistant polystyrene. The handle 50 defines an aperture 52 or internal chamber in which a trigger 60 is received, which trigger is biased towards an inactivated position shown in FIG. 1 by means of a spring element 66 constituted by a segment of a flexible plastic tubing. The internal chamber of the handle 50 is open to the interior of the housing of the dispensing device 10 through a hole 58 of the trough-shaped housing part 12. The trigger 60 is maintained in a pivotable position relative to the handle 50 by means of pins, one of which is shown in FIG. 2 and designated the reference numeral 64, protruding from the outer surface of the trigger 60, which pins are received in respective holes of the handle 50, one of which holes is shown in FIG. 2 and designated the reference numeral 54. As will be readily understood, the trigger 60 may pivot relative to the handle 50 relative to an axis of pivoting or rotation, which axis extends coaxially through the pins 64 and the holes 54. As the trigger 60 is pivoted or rotated relative to its axis of pivoting or rotation, an idler component 62 of the trigger 60 is also pivoted or rotated relative to the very same axis.

The pivoting of the trigger, and further of the idler component 62, is transmitted to a toothed rack 42 which is received within the trough-shaped housing part 12 resting on protruding parts 34 and 36 which are received within recesses of the toothed rack 42. The toothed rack is guided by the protruding parts 34 and 36 so as to allow a longitudinal displacement of the toothed rack 42 relative to the trough-shaped housing part 12 from a retracted position in which the toothed rack 42 is positioned adjacent to the rear wall 16 of the trough-shaped housing part 12 to an extracted position in which the toothed rack is shifted towards the partition wall 18 of the trough-shaped housing part 12.

The toothed rack 42 is, consequently, allowed to perform a reciprocating displacement or motion within the trough-shaped housing part 12 between its retracted position and its extracted position guided by the protruding parts 34 and 36. The reciprocating motion of the toothed rack 42 is generated as the trigger 60 is manually operated, as the idler component 62 of the trigger 60 cooperates with downwardly protruding parts 44 and 46 of the toothed rack 42, which downwardly protruding parts straddle the idler component 62. The toothed rack 42 is at its upper surface, i.e. opposite to the downwardly protruding parts 44 and 46, provided with teeth serving the purpose of propelling a propeller body 70, as will be discussed in greater detail below.

FIG. 2 also discloses in greater detail the syringes 80 and 81 which are of conventional structures, per se. The syringes 80 and 81 each comprises a syringe barrel 82 and 83, respectively, which syringe barrels are open at one end for receiving a cooperating piston rod and at the opposite end provided with dispensing tips 84 and 85, respectively. The syringe barrels 82 and 83 are at their open ends provided with outwardly protruding flanges 86 and 87. At their open ends, the syringe barrels 82 and 83 receive piston rods 88 and 89, respectively, which piston rods 88 and 89 define outer heads 90 and 91, respectively, and piston bodies 92 and 93, respectively, which piston bodies cooperate in sealing relationship with the inner cylindrical surface of the syringe barrels 82 and 83, respectively.

The syringes 80 and 81 are, as discussed above, received within the trough-shaped housing part 12 of the dispensing device 10 and are supported by the partition wall 18 of the trough-shaped housing part 12 as well as the front wall 28 of the cover or lid 22. The syringes 80 and 81 are further supported by the front wall 20 of the trough-shaped housing part 12 and arrested in position by recesses of the trough-shaped housing part 12 and of the cover or lid 22. Thus, the flanges 86 of the syringe barrel 82 of the syringe 80 is received within a recess 30 of the cover or lid 22 and a recess 39 provided within the trough-shaped housing part 12 in front of an upwardly protruding part 38. Similarly, the flange 87 of the syringe barrel 83 of the syringe 81 is arrested by means of a recess 41 provided within the interior of the trough-shaped housing part 12 and defined by a wall 40 thereof.

As mentioned above, the reciprocating displacement or motion of the toothed rack 42 is transmitted to the propeller body 70 for dispensing the fluids from the syringes 80 and 81. The propeller body 70 defines, as is evident from FIG. 2, a facial surface 72 and a recess 74 for cooperating with the heads 90 and 91, respectively, of the syringes 80 and 81, respectively. The propeller body 70 is further provided with oppositely arranged protruding parts 76 and 77 for cooperating with the teeth of the toothed rack 42 and teeth 30 provided at the inner surface of the cover or lid 22, respectively.

The dispensing device 10 functions in the following manner. It is assumed that the syringes 80 and 81 are positioned, as discussed above, within the trough-shaped housing part 12, and further that the head 90 of the syringe 80 is arranged in facial contact with the facial surface 72 of the propeller body 70 and that the head 91 of the syringe 81 is received within the recess 74 of the propeller body 70. It is further assumed that the cover 22 is in its closed position shown in FIG. 1.

As the cover 22 is closed, the teeth 30 of the inner surface of the cover or lid 22 are caused to mesh with the upwardly protruding part 77 of the propeller body 70, the downwardly protruding part 76 of which is also caused to mesh with the teeth 48 of the toothed rack 42. As the trigger 60 is manually operated, causing the idler component 62 to pivot or rotate relative to the axis of pivoting or rotation defined by the pins 64, the toothed rack 42 is displaced from its retracted position adjacent to the rear wall 16 towards its extracted position adjacent to the partition wall 18. As the toothed rack 42 is moved from its retracted position to its extracted position, as mentioned above, the propeller body 70 is also displaced towards the partition wall 18 and the front wall 28, causing a displacement of the piston rods 88 and 89 relative to the syringe barrels 82 and 83, respectively, of the syringes 80 and 81, respectively, further causing a dispensing of fluids from the syringes 80 and 81. As the trigger 60 is allowed to return to its inactivated position biased by the return element 66, the toothed rack 42 is also returned to its initial or retracted position. The teeth 30 of the cover or lid 22, however, prevent the propeller body 70 from being returned to its initial position and, consequently, prevent a bidirectional motion of the propeller body 70 which is allowed to move in unidirectional relation to the housing of the dispensing device 10, exclusively.

It is to be realized that the teeth 30 of the inner surface of the cover or lid 22 cooperate with the protruding part 77 of the propeller body 70 in a manner preventing a reversal of the displacement of the propeller body 70 relative to the trough-shaped housing part 12 of the dispensing device 10, and that the teeth 48 of the toothed rack 42 cooperate in a ratchet-like manner. It is further to be realized that in some instances the teeth 30 may be substituted by e.g. a frictional surface part of the cover or lid 22 or simply omitted, provided the cover or lid 22 itself provides adequate friction for preventing any reversal of the displacement of the propeller body 70.

It is, consequently, to be realized that unless the cover or lid 22 is closed to its closed position shown in FIG. 1, the manual activation of the trigger 60 causing a reciprocating displacement of the toothed rack 42 does not cause the propeller body 70 to be moved from its initial position arranged adjacent to the rear wall 16 towards the partition wall 18 as the toothed rack simply slides along the protruding part 76 at the lower side surface of the propeller body 70 instead of propelling the propeller body 70 towards the partition wall 18.

The propeller body 70 described above is provided with a single recess 74 for receiving the head 91 of the syringe 81. Alternatively or additionally, the propeller body 70 may be provided with a similar recess for receiving the head 90 of the syringe 80. Provided the propeller body 70 is provided with two recesses, such as the recess 74, the two recesses are preferably arranged so as to receive the cooperating heads of the two syringes from opposite sides of the propeller body, allowing a particularly easy and readily applicable mounting procedure. As is evident from FIG. 2, the dispensing device 10 is composed of a total of five components, viz. firstly, the trigger 60, secondly, the spring element 66, thirdly, a housing integrally comprising the handle 50, the trough-shaped housing part 12, and the cover or lid 22, fourthly, the toothed rack 42, and fifthly, the propeller body 70.

The above described first and presently preferred embodiment 10 of the dispensing device implemented in accordance with the teaching of the present invention is adapted to dispense specific and preset amounts of the fluids contained within the syringes 80 and 81, which amounts are determined by the distance of travel of the propeller body 70 as the propeller body 70 is advanced within the housing of the dispensing device 10 from its retracted position adjacent to the rear wall 16 towards the partition wall 18 and the front wall 28. The amounts of fluids dispensed from the syringes 80 and 81 are, consequently, independent of the position of the propeller body 70 relative to the housing of the dispensing device and proportional to the distance of travel of the propeller body 70 as the amount of fluids dispensed from the syringes 80 and 81 constitute a constant ratio, i.e. a specific and constant ratio defining the ratio of mixture of the two fluids.

Figure 3:
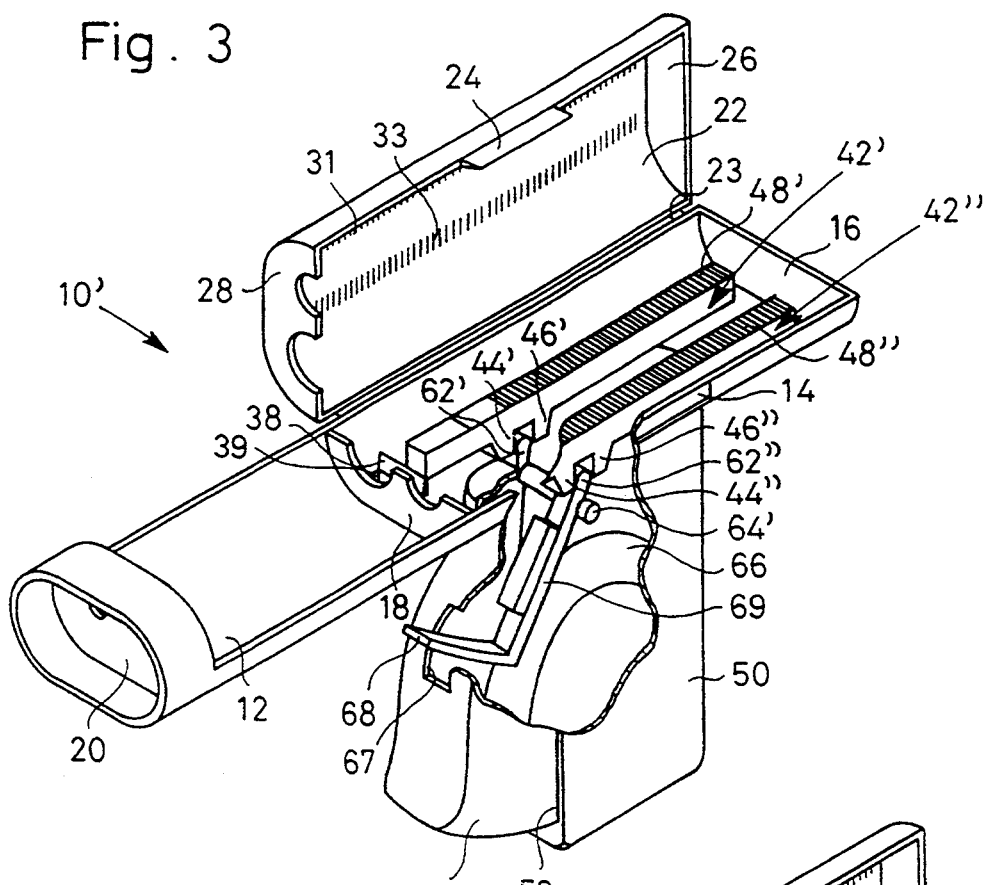
FIG. 3 is a partly cut-away, perspective and schematical view of a second embodiment of the dispensing device according to the present invention.
Figure 4:
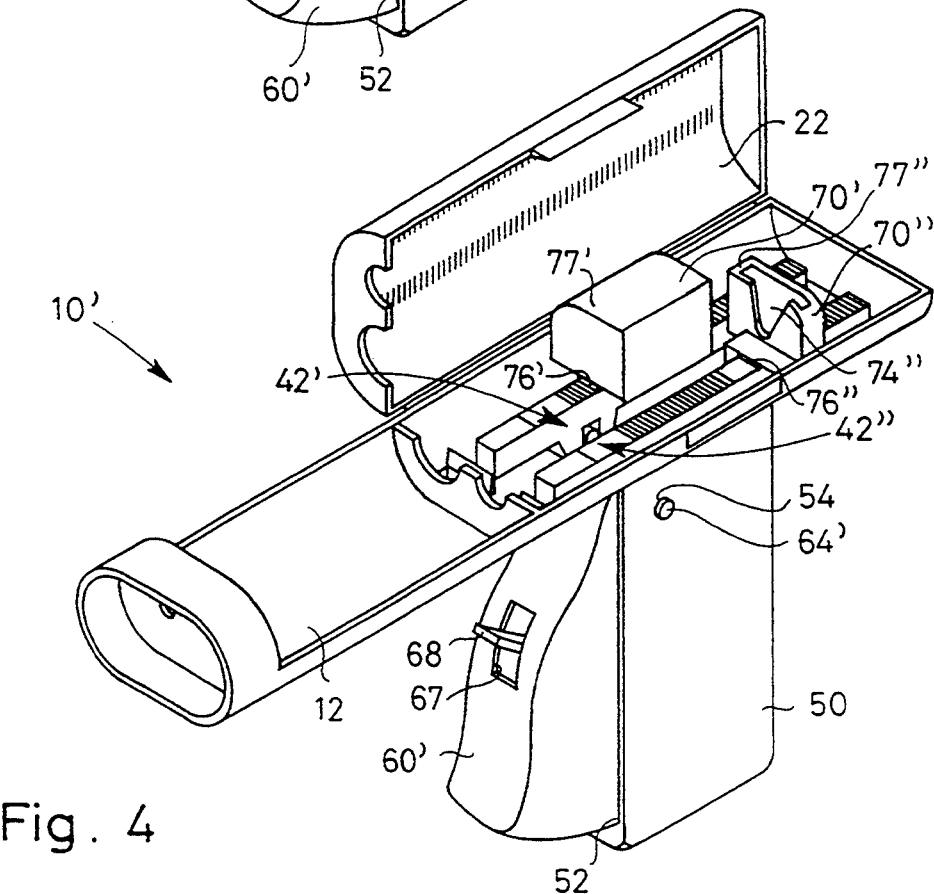
FIG. 4 is a perspective and schematical view of the second embodiment of the dispensing device according to the present invention also shown in FIG. 3.
Figure 5:
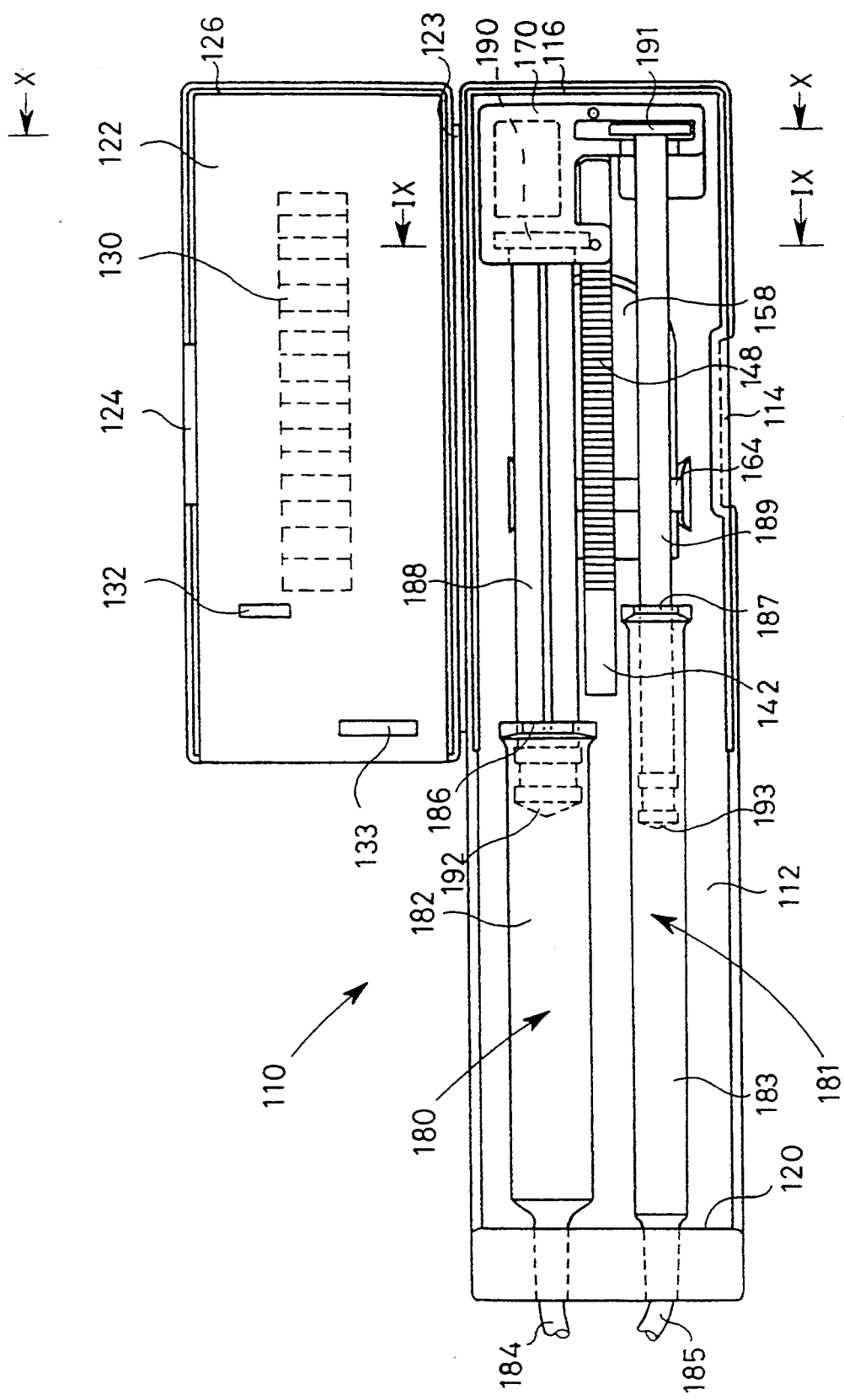
FIG. 5 is a top view of a third embodiment of the dispensing device according to the present invention.

In certain instances, it is necessary or desirable to alter the ratio or mixture of the two fluids or even to dispense a specific amount of one of the fluids exclusively without simultaneously dispensing any amount of the other fluid. In FIGS. 3 and 4, a slightly modified embodiment of the dispensing device implemented in accordance with the teaching of the present invention is shown, which dispensing device is designated by the reference numeral 10' in its entirety.

The protruding parts 76 and 77 are in the above described, presently preferred embodiment of the dispensing device located opposite one another in order to prevent from being the propeller body 70 jammed within the inner chamber defined within the trough-shaped housing component 12 as the cover or lid 22 is closed. The protruding parts 76 and 77 are in the above described embodiment located at the foremost end of the propeller body 70, however, the protruding parts 76 and 77 cooperating with the teeth 48 of the toothed rack 42 and the teeth 30 of the cover or lid 22, respectively, may alternatively be located at a central position or a rear position of the propeller body 70. Furthermore, more than a single set of protruding parts may be provided as well as low-frictional surface components may be provided, e.g. at the lower side surface of the propeller body 70, for assisting the propeller body 70 in moving along the teeth 48 of the toothed rack 42 as the toothed rack 42 is returned from its extracted position to its initial, retracted position.

The dispensing device 10' shown in FIGS. 3 and 4 basically differs from the dispensing device 10 shown in FIGS. 1 and 2 in that the propeller body 70 and the toothed rack 42 are substituted by separate propeller bodies and separate toothed racks cooperating with a respective syringe. Thus, in FIGS. 3 and 4, the toothed rack 42 shown in FIG. 2 is substituted by individual toothed racks 42' and 42" cooperating with respective propeller bodies 70' and 70" shown in FIG. 4, further cooperating with a respective syringe similar to the syringes 80 and 81 shown in FIGS. 1 and 2, however, omitted from FIGS. 3 and 4 for the sake of clarity. By the provision of separate toothed racks 42' and 42", the teeth 30 of the cover or lid 22 shown in FIG. 2 are substituted by separate teeth 33 and 31 cooperating or meshing with the propeller bodies 70' and 70", respectively, as the cover or lid 22 is closed to a position similar to the position of the cover 22 shown in FIG. 1. The toothed racks 42' and 42" comprise components similar to the components of the toothed rack 42 discussed above, which components are designated the marking ' and ", respectively, as compared to the reference numerals of the components of the toothed rack 42. Thus, the toothed racks 42' and 42" comprise protruding parts 44' and 44", respectively, and protruding parts 46' and 46", respectively, as well as teeth 48' and 48", respectively.

The handle 50 of the dispensing device 10' cooperates with a slightly modified trigger 60' which differs from the trigger 60 discussed above in that the trigger 60' is provided with an aperture 67 through which a sliding pin 68 protrudes. The trigger 60' is journalled relative to the handle 50 by means of a through-going shaft 64' which serves the same purpose as the pins 64 discussed above with reference to FIG. 2 and further the purpose of supporting a lever 69 which is integrally connected to the sliding pin 68 constituting an L-formed component. The trigger 60' is provided with an idler pin 62' integrally connected to the trigger 60', which idler pin 62' serves the same purpose as the idler component 62 of the trigger 60 discussed above. The idler component 62' cooperates, as is evident from FIG. 3, with the downwardly protruding parts 44' and 46' of the toothed rack 42'. The lever 69 is at its one end opposite to the sliding pin 68 provided with an idler pin 62" cooperating with the downwardly protruding parts 44" and 46" of the toothed rack 42".

Provided the syringes similar to the syringes 80 and 81 shown in FIG. 2 and described above are positioned within the trough-shaped housing part 12 of the dispensing device 10', and further provided that the propeller bodies 70' and 70" are positioned abutting the heads of the respective syringes, i.e. the heads 90 and 91 of the piston rods 88 and 89 of the syringes 80 and 81, respectively, shown in FIG. 2, and further provided that the cover or lid 22 is closed to a position similar to the position of the cover or lid 22 shown in FIG. 1, the dispensing device 10' is ready for use.

Like the propeller body 70 described above, the propeller bodies 70' and 70" are jammed between the teeth 33 and 31, respectively, of the cover or lid 22, and the inner side surface of the trough-shaped housing part 12. As the trigger 60' is activated, the trigger pivots or rotates round the shaft 64' causing the idler pin 62' to advance the toothed rack 42' from its initial retracted position shown in FIG. 4 to an extracted position adjacent to the partition wall 18. The toothed rack 42" is simultaneously advanced from its initial or retracted position shown in FIG. 3 towards the partition wall 18 as the trigger 60', the inner side surface of which abuts the lever 69, causes the lever 69 to rotate round the shaft 64' causing the toothed rack 42" to be advanced, and consequently causing the propeller body 70" to be advanced together with the propeller body 70' in a unidirectional motion towards the partition wall 18. The distance of advancement of the propeller body 70' is determined by the angular rotation of the trigger 60' relative to the handle 50. The propeller body 70 is advanced a distance which is proportional to the angle of rotation of the trigger 60' relative to the handle 50 determined by a fixed ratio of transmission, further determined by the length of the idler pin 62'. Similarly, the propeller body 70' is advanced a distance which is proportional to the angle of rotation of the trigger 60', however, determined by a ratio of transmission which may be altered as the length of the idler pin 62" may be altered by shifting the lever 69 to and from the toothed rack 42" by shifting the sliding pin 68 within the aperture, causing an alternation of the length of the idler pin 62" and consequently an alternation of the ratio of transmission.

The lever 69, however, further allows a separate dosing of a small amount of fluid from the syringe cooperating with the propeller body 70", i.e. a syringe similar to the syringe 81 shown in FIG. 2, as the outermost end of the sliding pin 68 may be activated without simultaneously activating the trigger 60'. By activating the outermost end of the sliding pin 68, causing the sliding pin 68 to be forced into the trigger 60', the lever 69 rotates round the supporting shaft 64' causing the toothed rack 42" to be advanced from its retracted position adjacent to the rear wall 16 towards the partition wall 18 and consequently causing the propeller body 70" to be advanced towards the partition wall 18 in the unidirectional motion described above, further causing dispensing of fluid from the syringe cooperating with the propeller body 70", exclusively.

In FIGS. 5–10, an alternative or third embodiment of the dispensing device implemented in accordance with the teaching of the present invention is shown, designated the reference numeral 110 in its entirety. The individual components of the dispensing device 110 shown in FIGS. 5–10 are designated the same reference numerals as similar components of the first embodiment 10 shown in FIGS. 1 and 2, however, added the prefix 1. No separate discussion of these components which have been described in great details above is therefore to be given. Below are only discussed the differences between the third embodiment 110 and the above described first and presently preferred embodiment 10 of the dispensing device according to the present invention shown in FIGS. 1 and 2.

Figure 6:
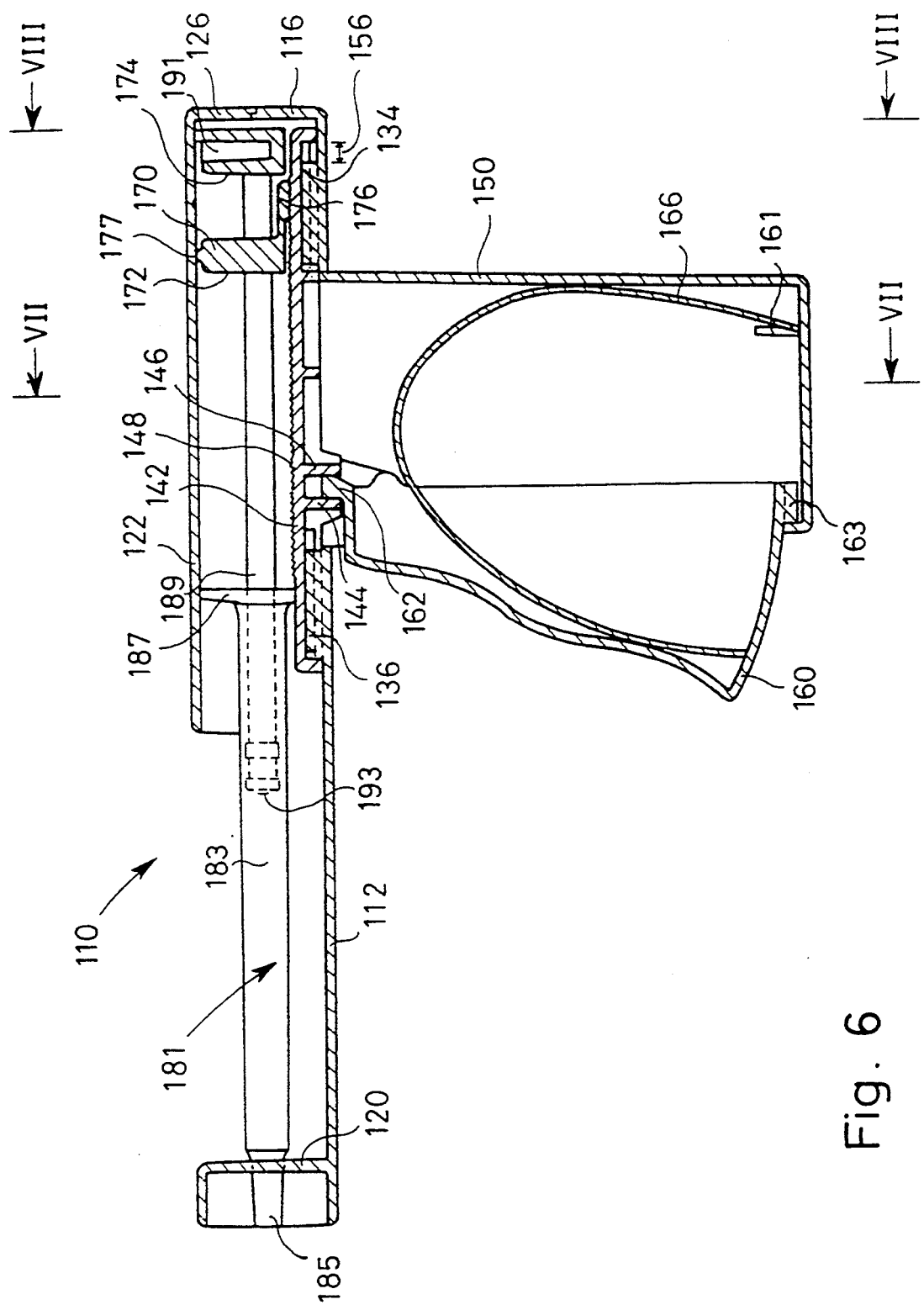
FIG. 6 is a vertical sectional view of the third embodiment of the dispensing device according to the present invention, along the line VI—VI of FIG. 5, FIGS. 7 and 8 are vertical sectional views of the third embodiment of the dispensing device according to the present invention also shown in FIGS. 5 and 6, along the lines VII—VII and VIII—VIII, respectively, of FIG. 6, FIGS. 9 and 10 are vertical sectional views, on a larger scale, of a component of the third embodiment of the dispensing device according to the present invention also shown in FIGS. 5-8, along the lines IX—IX and X—X, respectively, of FIG. 5.

As is evident from FIG. 6, the handle and trigger 150 and 160, respectively, of the dispensing device 110 is further provided with stops 161 and 163, respectively, limiting the rotational or pivotal motion of the trigger 160 relative to the handle 150. Also, as is evident from FIG. 6, the flexible plastic tubing constituting the spring element 66 described above is substituted by a spring leaf 166. The reference numeral 156 designates the maximum distance of travel of the toothed rack 142 relative to the trough-shaped housing part 112, which distance is determined by the upwardly protruding parts 134 and 136, serving the purpose of guiding the toothed rack 142 relative to the trough-shaped housing part 112 as the toothed rack is maintained in position in a snap engagement with the upwardly protruding parts 134 and 136. The trigger 160 is also, as compared to the trigger 60 discussed above, journalled in a somewhat different manner as the trigger is journalled relative to the handle 150 by means of a journalling shaft 164, the ends of which are provided with disc-shaped wheels which are received within guide tracks or recesses provided within the handle 50.

Figure 8:
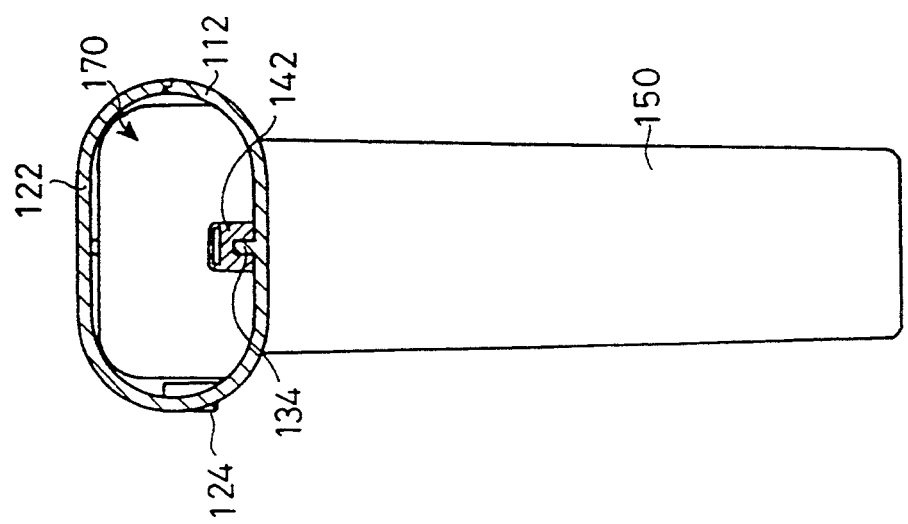
Figure 7:
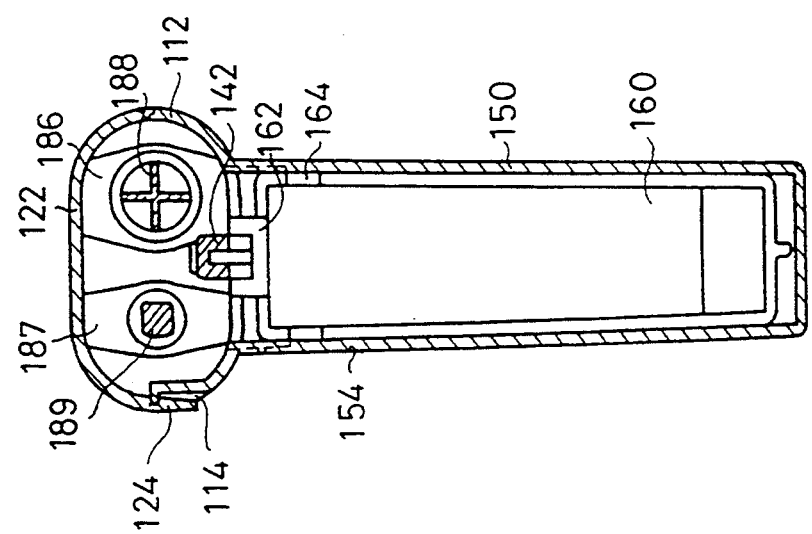

In FIGS. 7 and 8, vertical sectional views of the dispensing device 110 illustrate the internal structure of the dispensing device and the arrangement of the syringes 180 and 181 within the inner chamber defined by the trough-shaped housing part 112 and the cover or lid 122 as the cover or lid 122 is closed as shown in FIGS. 7 and 8.

Figure 10:
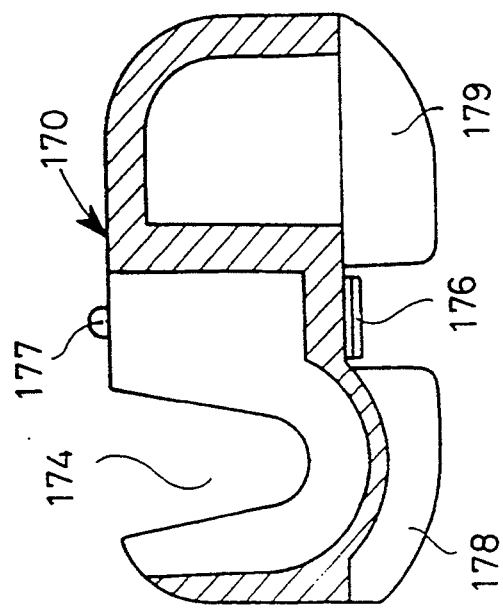
Figure 9:
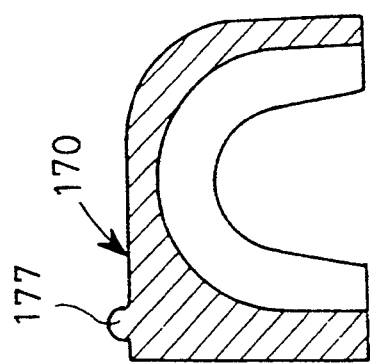

FIGS. 9 and 10 illustrate in greater detail and on a larger scale the propeller body 170 disclosing the downwardly and upwardly protruding parts 176 and 177, respectively, cooperating with the teeth 130 of the cover or lid 122 and the teeth 148 of the toothed rack 142, respectively. The recess 174 for cooperating with the head 191 of the syringe 181 is also disclosed together with a recess for cooperating with the head 190 of the syringe 180. Furthermore, two lower parts 178 and 179 are disclosed which, so to speak, constitute filling elements filling out the lower part of the chamber defined within the dispensing device, which lower parts straddle the toothed rack 142 and guide the propeller body 170 through the chamber in the longitudinal direction of the trough-shaped housing part 112, preventing the propeller body 170 from jamming within the inner space defined between the cover or lid 122 and the trough-shaped housing part 112 by preventing any tendency of tilting of the propeller body 170 relative to the longitudinal axis of displacement of the propeller body.

Figure 11:
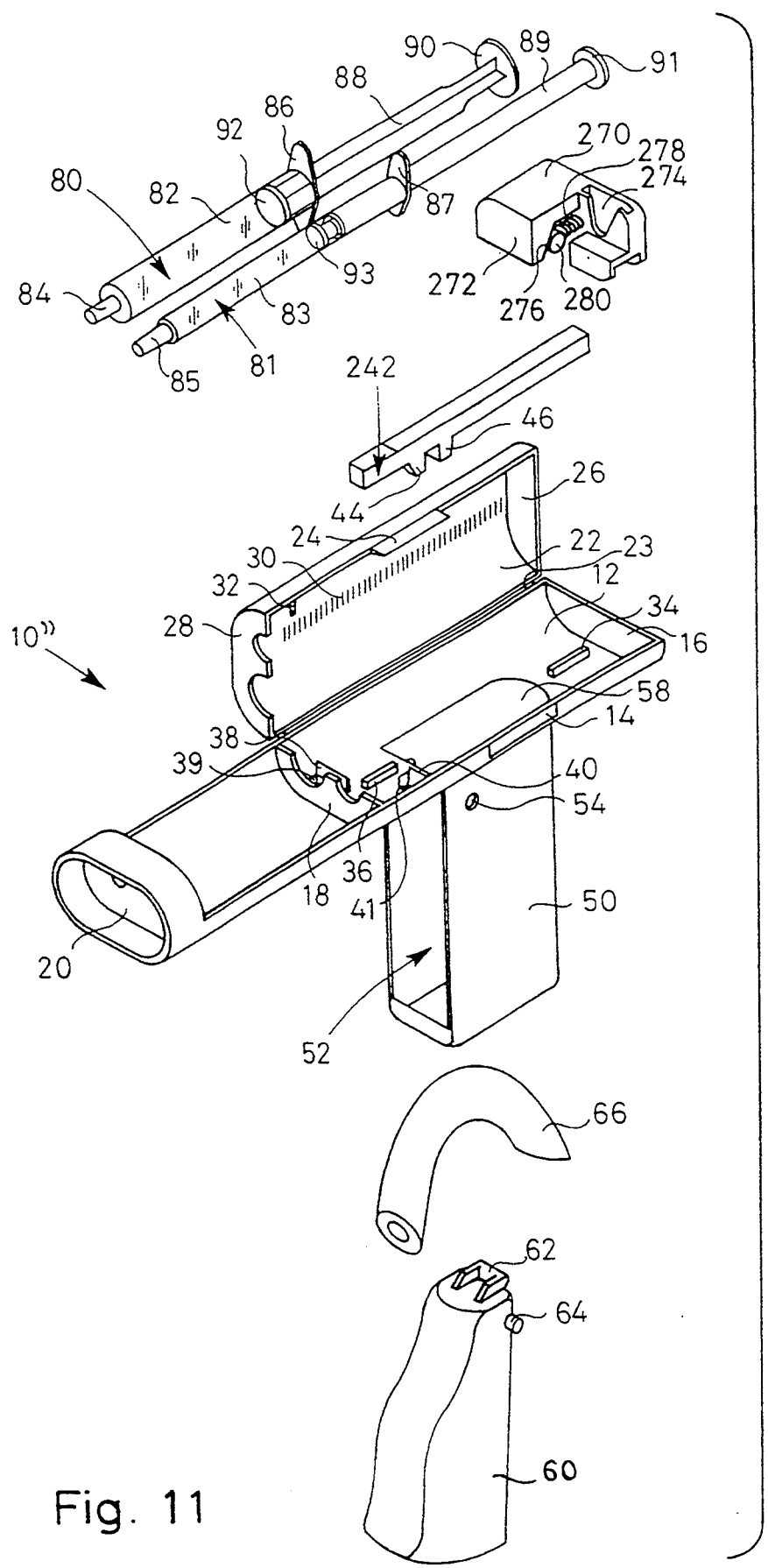
FIG. 11 is a perspective and schematic view, similar to the view of FIG. 2, of a fourth embodiment of the dispensing device according to the present invention.

In FIG. 11, a perspective and schematical view similar to the view of FIG. 2 is shown, disclosing a fourth embodiment of the dispensing device according to the present invention, designated the reference numeral 10" in its entirety. The fourth embodiment shown in FIG. 11 basically differs from the first embodiment shown in FIGS. 1 and 2 in that the ratchet-like uni-directional motion generating means constituted by the teeth 48 and the protruding part 76 of the toothed rack 42 and the propeller body 70, respectively, are substituted by frictional-like uni-directional motion generating means. The toothed rack 42 shown in FIGS. 1 and 2 is substituted by a rack 242 which is identical to the toothed rack 42 described above, except that the teeth 48 of the toothed rack 42 are omitted. The propeller body 70 shown in FIGS. 1 and 2 is substituted by a propeller body 270 which comprises a facial surface 272 and a recess 274 similar to the facial surface 72 and the recess 74 of the propeller body 70, shown in FIGS. 1 and 2. Instead of the downwardly protruding parts 76 of the propeller body 70 described above, the propeller body 270 shown in FIG. 11 is provided with a sloping surface 276 against which a cylindrical body 280 abuts, which cylindrical body is biased by a spring 278. The cylindrical body 280 is, so to speak, wedged between the upper plane surface of the rack 272 and the sloping surface 276 of the propeller body 270 as the rack 272 is moved forwardly guided by the protruding parts 34 and 36 from its initial, retracted position to its extracted position, i.e. towards the partition wall 18 which causes the propeller body 270 to be carried along with the rack 242, whereas the frictional engaging means constituted by the sloping surface 276 and the cylindrical body 280 allows to be the rack 242 moved rearwardly relative to the trough-shaped housing part 212 as the trigger 60 is forced to its initial inactivated position by the biasing element 66 without carrying along the propeller body 270 which is jammed within the inner chamber defined below the cover or lid 22 and retained in its position by the teeth 30 of the cover or lid 22. The cylindrical body 280 is preferably made from a material such as steel or similar metal or plastics material, i.e. a material of bigger hardness than the hardness of the rack 242.

Although the invention has been described above with reference to specific, at present preferred embodiments, the above detailed description and disclosure are by no means to be construed as limiting the protective scope of the present invention as defined in the appending claims. Thus, numerous modifications and amendments of the above described presently preferred embodiments are obvious to a person having ordinary skill in the art and are to be considered part of the present invention. Thus, the teachings of the present invention may readily be adapted to a manually operated dispensing device comprising more than two syringes, such as three or any arbitrary number of syringes in excess of two. Also, the ratchet-like unidirectional motion generating means may be substituted by any appropriate means fulfilling the same purpose, such as a frictional means or the like. It is further to be realized that although in the above described, presently preferred embodiments, the cover or lid constitutes the component serving the purpose of establishing engagement of the motion transmission means transmitting the motion of the trigger to the propeller body or bodies, any appropriate component of the dispensing device, or a separate component, such as a separate switch or locking component, may be employed for establishing the engagement of the transmission means for transmitting the motion of the trigger relative to the handle to the propeller body or propeller bodies for causing dispensing the fluids from the syringes.

EXAMPLE

A prototype implementation of the first and presently preferred embodiment of the dispensing device described above with reference to FIGS. 1 and 2 was made from the following components: the handle 50, the trough-shaped housing part 12, including the walls 16, 18, 20 and the protruding parts 34, 36, and 38, and the cover or lid 22 were cast from impact-proof polystyrene. The overall length of the trough-shaped housing part 12 was 156 mm, and the maximum width of the trough-shaped housing part 12 was 36 mm. The height of the handle 50 was 72 mm, and the cuts of the walls 18 and 28 were adapted to receive a conventional 1 ml syringe (the syringe 81) and a conventional 2 ml syringe (the syringe 80). The toothed rack 42 was cast from the same material as the housing, i.e. impact-proof polystyrene. The overall length of the toothed rack 42 was 73 mm, and the width of the toothed rack was 5.5 mm. The teeth 48 covered a length of 54 mm, and the downwardly protruding parts 44 and 46 defined a distance of 3 mm. The toothed rack 42 was at its lower side surface provided with recesses cooperating in a snap fitting with the protruding parts 34 and 36 of the trough-shaped housing component 12 for locking the toothed rack 42 in position relative to the trough-shaped housing component 12. The downwardly protruding parts 44 and 46 were located 50 mm and 47 mm, respectively, from the rearmost end of the toothed rack. The trigger 60 was, like the housing and the toothed rack 42, cast from impact-proof polystyrene. The spring element 66 was constituted by a 10 cm length of a PVC hose. The propeller body 70 was cast from impact-proof polystyrene.

I claim:

1. A dispensing device for dispensing at least two fluids, said dispensing device designed for receiving two or more syringes, each syringe comprising a syringe housing and a piston received within the syringe housing and defining together therewith a syringe chamber in which one of the fluids is confined, the piston being functionally coupled to a piston rod, the piston rod having a proximal end which is coupled to the piston and a distal end, said dispensing device comprising:
    a housing comprising at least one chamber which is at least partially enclosed and dimensioned to receive at least a portion of each of the syringes, said chamber having a front end and a back end spaced apart from one another along an axis;
    means cooperating with said housing for fixating each of the syringes such that at least a portion of the piston rod associated with each of the syringes lies within said chamber when the syringes are fixated to the housing;
    a manually operable trigger functionally attached to said housing and movable relative to the housing from an inactive position to an active position;
    a propeller received within said chamber and axially movable within said chamber at least from a first location proximate said back end of said chamber to a second location spaced apart from said first location in the direction of said front end of said chamber, said propeller further including means for engaging the syringe piston rods when the syringes are fixated to said housing;
    a selectively coupleable transmission between said trigger and said propeller, said transmission including a moving element and means for coupling said moving element to said trigger so that said moving element is moved in relation to said housing when said trigger is moved from said inactive to said active position,
    said transmission further including engagement means for selectively coupling said moving element functionally to said propeller such that said propeller may be moved relatively toward said front end of said chamber in response to said movement of said trigger; and switch means having an operative position and an inoperative position, said switch means being functionally coupled to said engagement means for selectively causing said engagement means to functionally engage said propeller to said moving element when said switch means is in the operative position, and for causing said engagement means to functionally disengage said propeller from said moving element when said switch means is in the inoperative position.

2. The dispensing device according to claim 1 wherein the chamber further comprises a movable cover having an open position and a closed position, and wherein said switch means comprises at least a portion of said cover such that said operative position of said switch means corresponds to said closed position of said movable cover, and said inoperative position of said switch means corresponds to said open position of said cover.

3. The dispensing device according to claim 2 wherein said moving element includes a propeller contact surface, and wherein said propeller includes a transmission contact surface which comprises said engagement means, and wherein said switch means further includes means for selectively moving said transmission contact surface and said propeller contact surface into functional engagement with each other only when said movable cover is in said closed position.

4. The dispensing device according to claim 1 wherein said propeller comprises separate propellers engaging the piston rods of each of the two or more syringes.

5. The dispensing device according to claim 4 wherein the transmission comprises separate transmissions cooperating with each of the propellers.

6. The dispensing device according to claim 5 wherein at least one of the separate transmissions is an adjustable transmission including means for adjusting the amount of movement of a first of said propellers relative to another of said propellers in response to movement of said trigger.

7. The dispensing device according to claim 1 wherein said transmission comprises a ratchet.

8. The dispensing device according to claim 7 wherein said moving element of said transmission means comprises a toothed rack and wherein said engagement means comprises one or more teeth on the propeller for cooperating with said toothed rack to generate said movement of the propeller toward the front end of the chamber.

9. The dispensing device according to claim 8 wherein said toothed rack is contained entirely within said chamber.

10. The dispensing device according to claim 1 wherein said propeller engages the distal ends of the piston rods of the syringes.

11. The dispensing device according to claim 10 wherein said propeller comprises a single propeller body provided with at least one recess for receiving at least one of the piston rods of said syringes.

12. The dispensing device according to claim 1 wherein the housing further includes a chamber bottom connecting said first and second ends of said chamber, and a handle functionally coupled to said chamber bottom such that the housing has an overall pistol-like configuration.

13. The dispensing device according to claim 12 wherein the trigger is attached to the handle.

14. The dispensing device according to claim 12 wherein said chamber comprises a movable cover having an open position and a closed position, and wherein said switch means comprises at least a portion of said cover such that said operative position of said switch means corresponds to said closed position of said movable cover, and said inoperative position of said switch means corresponds to said open position of said cover.

15. The dispensing device according to claim 14 wherein said moving element includes a propeller contact surface, and wherein said propeller includes a transmission contact surface which comprises said engagement means, and wherein said switch means further includes means for selectively moving said transmission contact surface and said propeller contact surface into functional engagement with each other only when said movable cover is in said closed position.

16. The dispensing device according to claim 12 wherein said propeller comprises separate propellers engaging the piston rods of each of two or more syringes.

17. The dispensing device according to claim 16 wherein the transmission comprises separate transmissions cooperating with each of the propellers.

18. The dispensing device according to claim 17 wherein at least one of the separate transmissions is an adjustable transmission including means for adjusting the amount of movement of a first of said propellers relative to another of said propellers in response to movement of said trigger.

19. The dispensing device according to claim 12 wherein said transmission comprises a ratchet.

20. The dispensing device according to claim 19 wherein said moving element of said transmission means comprises a toothed rack and wherein said engagment means comprises one or more teeth on the propeller for cooperating with said toothed rack to generate said movement of the propeller toward the front end of the chamber.

21. The dispensing device according to claim 20 wherein said toothed rack is contained entirely within said chamber.

22. The dispensing device according to claim 12 wherein said propeller engages the distal ends of the piston rods of the syringes.

23. The dispensing device according to claim 22 wherein said propeller comprises a single propeller body provided with at least one recess for receiving at least one of the piston rods of said syringes.

* * * * *

UNITED STATES PATENT AND TRADEMARK OFFICE
CERTIFICATE OF CORRECTION

PATENT NO. : 5,376,079
DATED : December 27, 1994
INVENTOR(S) : Niels E. Holm

It is certified that error appears in the above-indentified patent and that said Letters Patent is hereby corrected as shown below:

In column 3, line 57, after "syringes" insert --from--.

In column 11, line 32, delete "70'" and substitute --70"--.

In column 13, line 18, delete "to be".

In column 13, line 18, after "242" insert --to be--.

Col. 16,

In claim 20, lines 3-4, delete "engagment" and substitute --engagement--.

Signed and Sealed this

Seventh Day of May, 1996

Attest:

BRUCE LEHMAN

Attesting Officer    Commissioner of Patents and Trademarks